United States Patent [19]

Hubert et al.

[11] Patent Number: 4,621,158

[45] Date of Patent: Nov. 4, 1986

[54] METHOD FOR MAKING AMINES

[75] Inventors: Hans-Juergen Hubert, Hamm; Klaus D. Tillmetz, Olfen-Vinnum, both of Fed. Rep. of Germany

[73] Assignee: Schering Aktiengesellschaft, Bergkamen, Fed. Rep. of Germany

[21] Appl. No.: 767,823

[22] Filed: Aug. 21, 1985

[30] Foreign Application Priority Data

Aug. 31, 1984 [DE] Fed. Rep. of Germany ....... 3432015

[51] Int. Cl.4 ..................... C07C 85/08; C07C 85/02; C07C 85/18; C07C 85/06
[52] U.S. Cl. .................................. 564/473; 564/471; 564/479; 564/396; 564/397; 564/401; 564/402; 502/345
[58] Field of Search ............... 564/471, 473, 479, 396, 564/397, 401, 402; 502/345

[56] References Cited

U.S. PATENT DOCUMENTS

| 4,229,374 | 10/1980 | Slaugh et al. | 260/563 R |
| 4,409,399 | 10/1983 | Swift et al. | 564/473 |

FOREIGN PATENT DOCUMENTS

| 2844984 | 4/1979 | Fed. Rep. of Germany . |
| 3116395 | 5/1982 | Fed. Rep. of Germany . |
| 1554516 | 10/1979 | United Kingdom . |

*Primary Examiner*—Charles F. Warren
*Assistant Examiner*—Elizabeth A. Flaherty

[57] ABSTRACT

A method for making amines by reacting alcohols and/or aldehydes with primary and/or secondary amines or with ammonia in the presence of a catalyst at elevated temperature, and optionally at elevated pressure, in the liquid phase, the catalyst being an unsupported catalyst consisting of a combination of copper and tin compounds.

8 Claims, No Drawings

METHOD FOR MAKING AMINES

The present invention relates to a method for making amines by reacting long chain alcohols or aldehydes with primary amines, with secondary amines having the same or different substituents, or with ammonia at elevated pressure, and optionally under pressure, in the liquid phase in a reducing atmosphere in the presence of an unsupported catalyst.

Many catalyst systems suitable for this process have been described, as, for example, in U.S. Pat. No. 4,409,399, which gives a comprehensive summary of the pertinent prior art of liquid phase amination by the use of carrier systems or unsupported catalysts. In liquid phase amination, the alcohol or aldehyde is in the liquid phase while the ammonia or the primary or secondary amines are either in the liquid or the gaseous phase under the reaction conditions indicated.

It has been found that all catalyst systems named in the prior art for liquid phase amination processes have relatively poor activity and therefore must be used in large amounts at high pressures and temperature. According to U.S. Pat. No. 4,409,399, an unsupported catalyst system based on copper and nickel oxides or hydroxides exhibits improved activity in liquid phase amination.

This system offers the advantage of improved filterability over the prior art and is therefore easier to remove from the reaction mixture. However, some catalyst inevitably remains dissolved in the reaction product and since it would interfere with further reactions or could not be tolerated in certain end products it has to be separated by distillation of the amine component.

The distillation of long chain amines such as di-($C_{18}$-alkyl)methylamine, to the extent that they are amenable to distillation without decomposing, not only requires complex apparatus but also costly, time consuming and energy intensive process steps and, in addition, reduces the yield, often quite significantly. The same is essentially true of other purification methods such as filtration with filter aids and solvents, or extraction.

Published German patent application DOS 28 44 984 proposes a catalyst consisting of a Cu/Sn combination on a porous carrier. Before the catalyst can be used, it must be activated in hydrogen or ammonia at a temperature ranging from 250° C. to 600° C. for a period up to 24 hours.

However, in the preparation of mono- and di-alkylation products from primary amines in particular, the degree of alcohol conversion and the selectivity, as well as the activity of the catalysts attainable under the conditions of activation indicated, fall short of meeting practical requirements. Here, too, distillation of the reaction products is required.

The object of the present invention is to provide a method for making amines employing a catalyst which overcomes the drawbacks of the prior art and which is not only insoluble in the reaction products but exhibits improved activity, higher alcohol conversion, and increased selectivity with respect to the various alkylation stages, and particularly with respect to tertiary amines (dialkylation stage), even with primary amines as starting materials.

In accordance with the invention, this object is accomplished by a method for making amines using unsupported catalysts consisting of copper and tin compounds which are activated by means of organometallic compounds.

The invention thus relates to a method for making amines by reacting alcohols and/or aldehydes having up to 26 carbon atoms with primary and/or secondary amines having from 1 to 26 carbon atoms, or with ammonia, in the presence of a catalyst at elevated temperature, and optionally at elevated pressure, in the liquid phase, in the presence of an unsupported catalyst consisting of a combination of copper and tin compounds which preferably is activated prior to use, organometallic reducing agents in particular being used for activation.

Alcohols and/or aldehydes suitable for use with the process of the invention are compounds of the general formulas $$R(R^1)CHOH$$

and/or $$RC(O)H,$$

wherein R and $R^1$ may be the same or different and may be hydrogen, or linear or branched, saturated or unsaturated, aliphatic groups, or aromatic groups, suitably hydrocarbon groups. However, R and $R^1$ may optionally contain hetero atoms that are inert under amination conditions. R and $R^1$ together suitably have up to 25 carbon atoms, and more particularly from 5 to 21 carbon atoms, and preferably from 9 to 17 carbon atoms. Further R and $R^1$, together with the carbon atom to which they are bound, may form a ring which is optionally substituted and preferably five- or six-membered. Mixtures of the alcohols and/or aldehydes may also be used.

In accordance with the invention, primary alcohols or mixtures thereof wherein $R^1$ is hydrogen and R is a linear or branched aliphatic hydrocarbon group which has from 9 to 17 carbon atoms in the chain are preferred.

Examples of suitable alcohols are hexanol, octanol, nonanol, decanol, dodecanol, hexadecanol, octadecanol, 2-ethylhexanol, oleyl alcohol, ceryl alcohol, cyclopentanol, cyclohexanol, cyclooctanol, cyclodecanol, furfuryl alcohol, benzyl alcohol, phenethyl alcohol, the oxyalkylation products of these alcohols, especially with ethylene oxide and/or propylene oxide, and technical mixtures of $C_{12}$–$C_{15}$ alcohols with a linearity of from 40 to 80 percent.

In accordance with the invention, straight chain primary alcohols such as octanol, decanol, dodecanol, hexadecanol, octadecanol, and oleyl alcohol, are preferred.

In place of or in addition to the alcohols named, the corresponding aldehydes may be used. Preferred aldehydes are those corresponding to the alcohols which are preferably used in accordance with the invention.

The amines which are also used in accordance with the invention are compounds of the general formula $$R^2R^3NH,$$

where $R^2$ and $R^3$ may be the same or different and may be hydrogen, or linear or branched, saturated or unsaturated, aliphatic or araliphatic groups having 1 to 26 carbon atoms, preferably 1 to 18 carbon atoms, and are suitably hydrocarbon groups. However, $R^2$ and $R^3$ may optionally contain hetero atoms that are inert under amination conditions. $R^2$ and $R^3$ suitably have from 1 to 26 carbon atoms, and more particularly from 1 to 4 carbon atoms, and preferably from 1 to 2 carbon atoms. Further $R^2$ and $R^3$, together with the nitrogen atom to which they are bound, may form a ring which is preferably five- or six-membered and which optionally may be substituted, e.g. alkyl substituted, or may contain further hetero atoms. Suitable amines include monomethylamine, dimethylamine, monoethylamine, diethylamine, methylethylamine, methylbutylamine, piperidine, morpholine, pyrrolidine, 2-ethylhexylamine, dodecylamine, hexadecylamine, and the amines obtained from fatty acids having from 8 to 26 carbon atoms. In accordance with the invention, monomethylamine and dimethylamine are preferred. The amines named can be used alone or in admixture.

The unsupported catalyst system for the process of the invention is either a physical mixture of the particular salts or, preferably, a coprecipitate from an aqueous salt solution, obtained by the addition of suitable bases such as sodium hydroxide or carbonate, or potassium hydroxide or carbonate, until the requisite pH value is reached. After filtration, the metal hydroxides or oxides can be treated further in the usual manner, as by washing with water followed by oven drying or spray drying at temperatures ranging from 50° C. to 500° C., depending on the method used, for a period ranging from one to 24 hours.

The catalyst system contains copper and tin compounds, preferably the corresponding oxides and/or hydroxides, in a copper-to-tin molar ratio from 0.1 to 10, and preferably from 1.5 to 5.5.

Before the catalyst is used, it is advantageously activated, preferably with organometallic compounds, in an inert liquid medium, optionally at elevated temperature. In principle, any reducing organometallic compound can be employed as an activator, particularly organoaluminum or organomagnesium compounds of the formulas

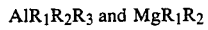

$AlR_1R_2R_3$ and $MgR_1R_2$ where $R_1$ and $R_2$ are the same or different linear or branched alkyl having 1 to 12 carbon atoms and $R_3$ is hydrogen or is similarly linear or branched $C_1$–$C_{12}$ alkyl.

Suitable organometallic compounds are those possessing reducing power, for example triethylaluminum, diethylaluminum ethoxylate, and particularly diisobutylaluminum hydride, butyloctylmagnesium, triisobutylaluminum, trimethylaluminum, di-isooctylaluminum hydride, tri-n-dodecylaluminum, methylbutylmagnesium, and di-n-octylmagnesium.

These compounds are used alone or in admixture in at least equivalent amounts, and preferably in a slight excess of from 0.1 to 0.2 equivalent, based on reducible groups in the catalysts.

As an inert liquid medium, aliphatic, cycloaliphatic, and aromatic hydrocarbons having a normal boiling point between 20° C. and 200° C. are suitably employed, e.g. materials commonly used as inert organic solvents.

Other activation methods, such as heating in a reducing atmosphere, commonly employed in the prior art, do not result in the desired properties which are essential for the process of the invention, such as improved activity and selectivity and reduced susceptibility to catalyst poisons which may be produced during the reaction. The high sedimentation rate, which makes it easy to separate the catalyst for repeated reuse, is also advantageous.

In carrying out the process of the invention, the alcohol or aldehyde to be reacted is charged to a heatable stirred vessel equipped for external gas circulation. The system is filled with hydrogen and heated to the reaction temperature of from 150° C. to 250° C., and preferably 170° C. to 230° C. The pressure is selected so that the starting material used will not boil. As a rule, the reaction of alcohols or aldehydes having boiling points above 150° C. is carried out at normal pressure or slightly elevated pressure, that is, about 1.2 to 2 bar. The activated catalyst, representing preferably from 0.2 to 3 percent by weight of the alcohol and/or aldehyde used, may be added before or after heating. The reaction is initiated by introducing the amine, the water of reaction formed being removed from circulation by condensation. Even fairly high amine concentrations in the circuit will not prove troublesome; however, it is preferable to introduce only as much amine as can be immediately consumed. This offers the advantage that in the overall balance the ratio of amine to alcohol or aldehyde can be held at about 1.0 to 1.1.

Just as uncritical, in comparison with the prior art processes, is the amount of hydrogen gas, which optionally may contain inert gases, that is circulated. Amounts ranging from 20 to 300 liters per kilogram of alcohol or aldehyde reagent and per hour are typical. On completion of the reaction, starting and intermediate products may be removed by means of carrier gas distillation and then recycled. Higher boiling secondary amines such as didodecylamine which are formed as intermediate products can be converted to the desired tertiary amine by the addition of an alcohol such as methanol after the amine addition is terminated. The reaction mixture is then cooled and the catalyst is separated by simple filtration and can be reused.

The catalyst can be reused many times without appreciable losses being observable so far as degree of conversion and selectivity are concerned.

The reaction products obtained with alcohol conversions of about 99 percent contain unwanted amination by-products only in amounts of less than 2 percent and thus have a purity that is sufficiently high for most subsequent processes, for example the production of quaternary ammonium compounds, so that distillation can usually be dispensed with.

A further advantage of the catalyst used in accordance with the invention is that it will not reduce, even in the presence of hydrogen, such multiple bonds as may be present, so that products with unaltered high iodine numbers are obtained.

A better understanding of the present invention and of its many advantages will be had by referring to the following Examples, given by way of illustration.

PREPARATION OF CATALYST

Catalyst I

To prepare a catalyst, 200.1 g of cupric hydroxide and 156.8 g of stannous oxide are finely powdered together and suspended in 1500 ml of toluene. (Procedure A). The catalyst has a molar copper-to-tin ratio of 1.76. (Catalyst I).

Activation of catalyst

To activate this catalyst, the suspension of Catalyst I is heated to 100° C. and 314 g of diisobutylaluminum hydride (DIBAH) are added dropwise with vigorous stirring. This addition is controlled so that the toluene boils lightly. After all the DIBAH has been added, the suspension is held at the boiling temperature for 1 hr. It is then allowed to cool to room temperature while being stirred and the stirrer is then turned off so that the finely dispersed catalyst is able to settle. The supernatant toluene is then decanted and a suspension is made with 500 ml of toluene. After renewed sedimentation, washing and sedimentation are repeated with 500 ml of toluene. This process is repeated two more times. While moist with toluene, the active catalyst can be handled without difficulty.

Catalyst II 155.5 g of cupric hydroxide and 41.4 g of stannous oxide are intimately mixed as in Example 1. (Procedure A). They are then activated with 195.5 g of DIBAH as described in Example 1. The molar copper-to-tin ratio is 5.2.

Catalyst III 9.6 wt. % stannous formate is added to a 30% solution of cupric nitrate in water. From this solution, a catalyst precursor is precipitated with 30% potassium carbonate solution at 60° C. On completion of precipitation, the precipitate is filtered off and the filter cake is washed neutral and free of nitrate. This is followed by thorough drying at 60° C. in vacuum. (Procedure B). 186 g of this catalyst are activated with 213 g of DIBAH as described in Example 1. The molar copper-to-tin ratio is 3.5.

Catalyst IV 155.5 g of cupric hydroxide and 22.5 g of stannous oxide are intimately mixed (Procedure A) and activated with 181 g of DIBAH, as described in Example 1. The molar copper-to-tin ratio is 9.55.

Catalyst V 13.9 wt. % stannous formate is added, to a 30% solution of cupric nitrate in water, as described under Catalyst III. (Procedure B). The further working up is as there described. 245 g of this catalyst are then activated with 325 g of triisobutylaluminum (TIBA) as described in Example 1. The molar copper-to-tin ratio is 2.4.

Catalyst VI 200 g of cupric hydroxide and 157 g of stannous oxide are intimately mixed (Procedure A) and activated as described in Example 1 but with 680 g of butylcotylmagnesium (B0MAG) in place of DIBAH. The copper-to-tin is 1.76.

Catalyst VII 15.5 g of cupric hydroxide and 135 g of stannous oxide are intimately mixed and activated with 120 g of DIBAH, as described in Example 1. The copper-to-tin ratio is 0.16.

Catalyst VIII 5.0 kg of cupric hydroxide and 2.8 kg of stannous oxide are intimately mixed, suspended in 60 liters of toluene, and activated with 7.05 kg of DIBAH as described in Example 1. The molar copper-to-tin ratio is 2.47.

Catalyst IX 216 g of copper-(I)-cyanide and 237 g of tin-(II)-acetate were thoroughly mixed as in Example 1 (method A) and suspended in 1,500 ml of pentane. 700 g of triethylaluminum (TEA) were added to this suspension at room temperature with good stirring and with cooling. After all of the TEA had been added, the mixture was stirred for an additional two hours. Further treatment for removal of the unreacted TEA was carried out as described earlier for Catalyst I, "Activation of Catalyst".

Catalyst X

This catalyst was prepared by the method used for Catalyst VIII except that activation was carried out at 140° C. in decalin as an inert solvent.

Catalyst XI

Catalyst VI was activated as in Example 1 using the different organometallic compounds described below:
(A) Trimethylaluminum (TMA)
(B) Di-iso-octylaluminum hydride (DOAH)
(C) Tri-n-dodecylaluminum (TDA)
(D) Methyl-butylmagnesium (MEBUMG)
(E) Di-n-octyl magnesium ($OC_2MG$).
These organometallic compounds were used in an excess of 0.1 equivalent part calculated on the equivalent parts of reducible groups in the catalyst.

TABLE

CATALYST PREPARATION

| Catalyst | Preparation procedure | Composition mols Cu/mols Sn | Activator |
|---|---|---|---|
| I | A | 1.76 | DIBAH |
| II | A | 5.2 | DIBAH |
| III | B | 3.5 | DIBAH |
| IV | A | 9.55 | DIBAH |
| V | B | 2.4 | TIBA |
| VI | A | 1.76 | BOMAG* |
| VII | A | 0.16 | DIBAH |
| VIII | A | 2.47 | DIBAH |

*Registered trademark of Schering AG.

AMINATION

Example 1

700 g lauryl alcohol are charged to a 3-liter agitator with gas sparger. The reactor is then filled with hydrogen. With the agitator turned on, a hydrogen circulation of 71 liters/hour/kg alcohol is established. An additional 29 liters/hour/kg alcohol are circulated through the apparatus. The contents of the reactor are then heated to the reaction temperature of 180° C. Once that temperature has been reached, 13.5 g of Catalyst I are added and the addition of monomethylamine (MMA) is begun. The water of reaction formed is removed from the circulating gas by condensation. After 6.5 hours an alcohol conversion of 99.8% is obtained. The tertiary amine content is 85 wt. %, 95.6 wt. % of which is methyldidodecylamine. The catalyst is separated by filtration.

The Examples which follow are carried out analogously.

Example 2a

Reactor volume: 3 liters

Alcohol: 700 g of lauryl alcohol
Hydrogen circulation: 100 liters/hour/kg of alcohol
Hydrogen addition: 29 liters/hour/kg of alcohol
Amine: Monomethylamine
Temperature: 220° C.
Catalyst: 12.0 g of catalyst V After 4 hours, the alcohol conversion is 99.7%, and the tertiary amine content is 89.5%, 96.8 wt. % of which is methyldidodecylamine.

Example 2b

On completion of the reaction according to Example 2a, the amine addition is stopped while hydrogen circulation is maintained at the reaction temperature of 220° C. Under these conditions, the readily volatile constituents such as secondary methyldodecylamine, dimethyldodecylamine, residual lauryl alcohol, and some of the by-products which do not contain nitrogen are distilled off and removed from circulation by condensation. The tertiary amine content of the product rises to 91.1 wt. %, 97.9 wt. % of which is methyldidodecylamine.

Example 2c

Methanol is added at the reaction temperature of 220° C. to the circulating product prepared according to Example 2b and still containing the catalyst. Under these conditions, the secondary didodecylamine still contained in the products reacts further to yield the desired methyldidodecylamine. The tertiary amine content rises to 93.7 wt. %, 98.0 wt. % of which is methyldidodecylamine.

Example 3

Reactor volume: 30 liters
Alcohol: 7 kg of lauryl alcohol
Hydrogen circulation: 500 liters/hour/kg of alcohol
Hydrogen addition: 7 liters/hour/kg of alcohol
Amine: Dimethylamine (DMA)
Temperature: 210° C.
Catalyst: 102.9 g catalyst III After 11 hours, the alcohol conversion is 99.3% while the tertiary amine content is 97.9 wt. %, 95.0 wt. % of which is dimethyldodecylamine.

Example 4

Reactor volume: 3 liters
Alcohol: 700 g of lauryl alcohol
Hydrogen circulation: 71 liters/hour/kg of alcohol
Hydrogen addition: 29 liters/hour/kg of alcohol
Amine: Dimethylamine
Temperature: 210° C.
Catalyst: 18.0 g catalyst I After 9 hours, the alcohol conversion is 99.8% while the tertiary amine content is 97.0 wt. %, 95.2 wt. % of which is dimethyldodecylamine.

Simple distillation yields dimethyldodecylamine of a purity of 98.7%.

Comparative Example 1

This example is run like Example 4.
Reactor volume: 3 liters
Alcohol: 700 g of lauryl alcohol
Hydrogen circulation: 67 liters/hour/kg of alcohol
Hydrogen addition: 22 liters/hour/kg of alcohol
Amine: Dimethylamine
Temperature: 210° C.
Catalyst: 9.3 g copper chromite After 7 hours, the alcohol conversion is 93.9% while the tertiary amine content is 75.3 wt. %, 94.6 wt. % of which is dimethyldodecylamine.

Comparative Example 2

This example is run like Example 4. However, the catalyst is added already at room temperature. The batch is heated in the hydrogen stream to reaction temperature.
Reactor volume: 3 liters
Alcohol: 900 g of lauryl alcohol
Hydrogen circulation: 67 liters/hour/kg of alcohol
Hydrogen addition: 22 liters/hour/kg of alcohol
Amine: Dimethylamine
Temperature: 210° C.
Catalyst: 9.0 g $Cu(OH)_2 + Ni(OH)_2$ After 4.3 hours, the alcohol conversion is 99.6% while the tertiary amine content is 70.6 wt. %, 81.9 wt. % of which is dimethyldodecylamine.

Comparative Example 3

This example is run like Example 4. The catalyst is added only at the reaction temperature.
Reactor volume: 3 liters
Alcohol: 900 g of lauryl alcohol
Hydrogen circulation: 67 liters/hour/kg of alcohol
Hydrogen addition: 28 liters/hour/kg of alcohol
Amine: Dimethylamine
Temperature: 210° C.
Catalyst: 9.0 g $Cu(OH)_2 + Ni(OH)_2$ Cu/Ni=1.72

After 3 hours, the alcohol conversion is 99.8% while the tertiary amine content is 93.9 wt. %, 92.3 wt. % of which is dimethyldodecylamine.

Comparisons with Example 4

| | Catalyst | Alcohol Conversion | tert. amines | Product Compostion |  |  |
|---|---|---|---|---|---|---|
| | | | | $Me_2NR^*$ | $R_2NMe^*$ | $R_3N^*$ |
| | | | | (weight percent) | | |
| Comp. Example | | | | | | |
| 1 | Cu/Cr | 94.6 | 75.3 | 94.6 | 2.7 | 2.7 |
| 2 | Cu/Ni | 99.6 | 70.6 | 81.9 | 16.9 | 1.2 |
| 3 | Cu/Ni | 99.8 | 93.0 | 82.3 | 16.5 | 1.2 |
| Example | | | | | | |
| 4 | Cu/Sn | 99.8 | 97.0 | 95.2 | 4.5 | 0.3 |

*Me = Methyl group
N = Nitrogen
R = Residue of alcohol used

Example 5

Reactor volume: 3 liters
Alcohol: 700 g of lauryl alcohol
Hydrogen circulation: 71 liters/hour/kg of alcohol
Hydrogen addition: 29 liters/hour/kg of alcohol
Amine: Dimethylamine
Temperature: 210° C.
Catalyst: 12.0 g of Catalyst III After 7 hours, the alcohol conversion is 99.5% while the tertiary amine content is 96.1 wt. %, 93.0 wt. % of which is dimethyldodecylamine.

Example 6

Reactor volume: 3 liters
Alcohol: 700 g of lauryl alcohol
Hydrogen circulation: 71 liters/hour/kg of alcohol
Hydrogen addition: 29 liters/hour/kg of alcohol Amine: Dimethylamine
Temperature: 190° C.
Catalyst: 14.0 g of Catalyst VI After 10 hours, the alcohol conversion is 99.7% while the tertiary amine content is 95.0 wt. %, 97.1 wt. % of which is dimethyldodecylamine.

Example 7

Reactor volume: 3 liters
Alcohol: 700 g of lauryl alcohol
Hydrogen circulation: 70 liters/hours/kg of alcohol
Hydrogen addition: 30 liters/hour/kg of alcohol
Amine: Dimethylamine
Temperature: 190° C.
Catalyst: 12.0 g of Catalyst IV After 7 hours, the alcohol conversion is 99.7% while the tertiary amine content is 88.4 wt. %, 96.7 wt. % of which is dimethyldodecylamine.

Example 8

Reactor volume: 3 liters
Alcohol: 700 g of stearyl alcohol
Hydrogen circulation: 69 liters/hour/kg of alcohol
Hydrogen addition: 30 liters/hour/kg of alcohol
Amine: Monomethylamine
Temperature: 230° C.
Catalyst: 15.0 g of Catalyst II After 6 hours, the alcohol conversion is 99.4% while the tertiary amine content is 89.0 wt. %, 91.6 wt. % of which is distearylmethylamine.

TABLE

| | | Amination | | |
|---|---|---|---|---|
| Example | Catalyst | Alcohol | Amine | Temperature (°C.) |
| 1 | I | Lauryl | MMA* | 180 |
| 2a,b,c | V | Lauryl | MMA | 220 |
| 3 | III | Lauryl | DMA** | 210 |
| 4 | I | Lauryl | DMA | 210 |
| 5 | III | Lauryl | DMA | 210 |
| 6 | VI | Lauryl | DMA | 190 |
| 7 | IV | Lauryl | DMA | 190 |
| 8 | II | Stearyl | MMA | 230 |

| Example | Alcohol conversion | Tertiary amine content (wt. %) | Composition of tertiary amines | | |
|---|---|---|---|---|---|
| | | | Me$_2$NR (wt. %) | R$_2$NMe (wt. %) | R$_3$N (wt. %) |
| 1 | 99.8 | 85.0 | 2.5 | 95.6 | 1.9 |
| 2a | 99.7 | 89.5 | 2.0 | 96.8 | 1.2 |
| 2b | 99.7 | 91.1 | 0.9 | 97.9 | 1.2 |
| 2c | 99.7 | 93.7 | 0.8 | 98.0 | 1.2 |
| 3 | 99.3 | 97.9 | 95.0 | 4.8 | 0.2 |
| 4 | 99.8 | 97.0 | 95.2 | 4.5 | 0.3 |
| 5 | 99.5 | 96.1 | 93.0 | 6.8 | 0.2 |
| 6 | 99.7 | 95.0 | 97.1 | 2.1 | 0.8 |
| 7 | 99.7 | 88.4 | 96.7 | 2.8 | 0.5 |
| 8 | 99.4 | 89.0 | 7.4 | 91.6 | 1.0 |

*Monomethylamine
**Dimethylamine

Example 9

Reactor volume: 300 liters
Alcohol: 170 kg of dodecyl alcohol
Hydrogen circulation: 120 liters/hour/kg of alcohol
Hydrogen addition: 0.1 liters/hour/kg of alcohol
Amine: Monomethylamine
Temperature: 200° C.
Catalyst: 8.1 kg of Catalyst VIII The reaction is carried out in a 300-liter agitator with external gas circulation. The amine is added in nearly stoichiometric amounts, that is it is metered in so that the amine concentration in the circulating gas does not exceed 0.5 volume percent (Examples 9a to 9f) or 1.5 volume percent (Examples 9g to 9i). For determination of the amine content, a small gas stream of 0.1 liter/hour/kg alcohol is withdrawn from circulation and routed to an infrared measuring device. This slight gas loss incurred for measuring purposes is made up by fresh hydrogen. On completion of the reaction, the catalyst is separated from the product by sedimentation and reused without the addition of fresh catalyst. The reaction is completed after 8 to 9 hours. The product is colorless and free of dissolved traces of metal.

TABLE

| Example | MMA in circulating gas (vol. %) | Alcohol conversion (%) | Tertiary amine content (wt. %) | Composition of tertiary amines | | |
|---|---|---|---|---|---|---|
| | | | | R$_2$Me (wt. %) | RNMe$_2$ (wt. %) | R$_3$N (wt. %) |
| 9a | 0.5 | 99.3 | 93.0 | 98.0 | 0.8 | 1.2 |
| 9b | 0.5 | 99.2 | 95.5 | 97.9 | 0.4 | 1.7 |
| 9c | 0.5 | 99.6 | 93.5 | 97.2 | 0.4 | 2.4 |
| 9d | 0.5 | 99.3 | 94.0 | 97.6 | 0.4 | 2.0 |
| 9e | 0.5 | 99.5 | 94.1 | 98.3 | 0.3 | 1.4 |
| 9f | 0.5 | 99.5 | 93.3 | 98.4 | 0.3 | 1.3 |
| 9g | 1.5 | 99.4 | 93.0 | 97.8 | 0.8 | 1.4 |
| 9h | 1.5 | 99.5 | 93.5 | 98.4 | 0.5 | 1.1 |
| 9i | 1.5 | 99.2 | 94.2 | 97.7 | 1.5 | 1.0 |

Example 10

Reactor volume: 3 liters
Alcohol: 500 g of isotridecyl alcohol (mixture of isomers)
Hydrogen circulation: None
Hydrogen addition: 150 liters/hour/kg of alcohol
Amine: Monomethylamine
Temperature: 210° C.
Catalyst: 23 g of Catalyst VIII The reaction is carried out in a 3-liter agitator without hydrogen circulation. The amine concentration at the inlet is 6.25 volume percent. The reaction is terminated after 6 hours. The product contains 84.6 wt. % tertiary dialkylmethylamine, in addition to 14.6 wt. % of the alcoholic mixture of isomers.

Example 11

Reactor volume: 3 liters
Alcohol: 500 g of benzyl alcohol
Hydrogen circulation: 60 liters/hour/kg of alcohol
Hydrogen addition: 60 liters/hour/kg of alcohol
Amine: Monomethylamine
Temperature: 180° to 210° C.
Catalyst: 20 g of Catalyst VIII The reaction is carried out in a 3-liter agitator with gas circulation at normal pressure. The temperature is initially 180° C. since the contents of the reactor boil vigorously and foam as the reaction sets in. As the reaction proceeds, a temperature of 210° C. is reached. After 8 hours, the alcohol conversion is 99.2%. The product contains 73.6 wt. % dibenzylmethylamine and 15.5 wt. % benzaldehyde.

Example 12

Reactor volume: 3 liters
Mixture charged: 500 g, composed of 36.6 wt.% of dodecylaldehyde, 36.4 wt.% of tetradecylaldehyde, 27.0 wt.% of tetradecyl alcohol
Hydrogen circulation: None Hydrogen addition: 150 liters/hour/kg of mixture charged
Amine: Monomethylamine
Temperature: 210° C.
Catalyst: 25 g of Catalyst VIII After 6 hours, 99.1% conversion of the mixture charged is obtained. The product consists to the extent of 85.6 wt. % of a mixture of dialkylmethylamines of chain lengths $C_{12}$ and $C_{14}$.

Example 13

Reactor volume: 30 liters
Alcohol: 12 kg of stearyl alcohol
Hydrogen circulation: 290 liters/hour/kg of alcohol
Hydrogen addition: 1.2 liters/hour/kg of alcohol
Amine: Monomethylamine
Temperature: 200° C.
Catalyst: 360 g of Catalyst VIII The amine content in the circulation is held at 1 to 2 volume percent. After 6 hours, the alcohol conversion is 99.1% while the tertiary amine content is 97.6 weight percent. 95.4 weight percent thereof is distearylmethylamine.

Example 14

Reactor volume: 30 liters
Alcohol: 12 kg of tallow alcohol (soft tallow)*
*) "Tallow alcohol" is a technical mixture of $C_{16}$-to-$C_{18}$ alcohols with a minor amount of $C_{14}$ alcohols containing also unsaturated alcohols (iodine number 48).
Hydrogen circulation: 200 liters/hour/kg of alcohol
Hydrogen addition: 1.0 liters/hour/kg of alcohol
Amine: Monomethylamine
Temperature: 200° C.
Catalyst: 360 g of Catalyst VIII The amine content in the circulation is held at 1 to 2 volume percent. After 5.5 hours, the alcohol conversion is 99.7% while the tertiary amine content is 92.3 weight percent. 91.6 weight percent thereof is dialkylmethylamine.

Example 15

Reactor volume: 30 liters
Alcohol: 12 kg of oleyl alcohol (iodine number 85)
Hydrogen circulation: 275 liters/hour/kg of alcohol
Hydrogen addition: 1.1 liters/hour/kg of alcohol
Amine: Monomethylamine
Temperature: 200° C.
Catalyst: 360 g of Catalyst VIII After 5 hours, the alcohol conversion is 99.5% while the tertiary amine content is 94.8 wt. %. 92.5 wt. % thereof is dioleylmethylamine.

Example 16

Reactor volume: 3 liters
Alcohol: 700 g of lauryl alcohol
Hydrogen circulation: None
Hydrogen addition: 80 liters/hour/kg of alcohol
Amine: Ammonia
Temperature: 220° C.
Catalyst: 22 g of Catalyst VIII After 5 hours, the alcohol conversion is 98% while the tertiary amine content is 93.6 wt. %, 27 wt. % of which is dilaurylamine.

Example 17

Reactor volume: 3 liters
Alcohol: 700 g of lauryl alcohol
Hydrogen circulation: 70 liters/hour/kg of alcohol
Hydrogen addition: 30 liters/hour/kg of alcohol
Amine: n-Butylamine
Temperature: 210° C.
Catalyst: 22 g of Catalyst VIII After 5 hours, the alcohol conversion is 99.3% while the tertiary amine content is 92 wt. %, 96.9 wt. % of which is butyldilaurylamine.

Example 18

Reactor volume: 3 liters
Alcohol: 700 g of 1-hexanol
Hydrogen circulation: 70 liters/hour/kg of alcohol
Hydrogen addition: 30 liters/hour/kg of alcohol
Amine: Monomethylamine
Temperature: 180° C.
Catalyst: 22 g of Catalyst VIII After 8 hours, the alcohol conversion is 99.1% while the tertiary amine content is 90 wt. %, 96.5 wt. % of which is dihexylmethylamine.

Example 19

Reactor volume: 3 liters
Alcohol: 700 g of decyl alcohol
Hydrogen circulation: 70 liters/hour/kg of alcohol
Hydrogen addition: 30 liters/hour/kg of alcohol
Amine: Dimethylamine
Temperature: 210° C.
Catalyst: 22 g of Catalyst VIII After 8 hours, the alcohol conversion is 99.5% while the tertiary amine content is 92.1 wt. %, 96.8 wt. % of which is decyldimethylamine.

Example 20

537 g of oleyl amine and 256 g of 2-ethylhexanol were reacted in a three-liter stirred vessel in the presence of 40 g of Catalyst X at 215° C. and at a pressure of 2.0 bar. The water of reaction formed was removed by condensation from the hydrogen circulation of 20 liter/hour/kg of alcohol. The reaction was completed in nine hours. The reaction product contains 94 percent of dioctyloleyl amine.

Example 21

540 g of stearyl alcohol were reacted with 257 g of 2-ethylhexyl amine in a three-liter stirred vessel in the presence of 40 g of Catalyst X at 215° C. and under a pressure of 2.0 bar. The water of reaction formed was removed by condensation from the hydrogen circulation of 200 liter/hour/gram of alcohol. The reaction was completed after nine hours. The reaction product contains 95.2 percent of distearyl-2-ethyl-hexyl amine.

Example 22

The various catalysts XI(A)-(E) were employed for amination in a method corresponding to Example 6. The following results were obtained:

| Catalyst | Alcohol Conversion | Content of Tert. Amine (Weight Percent) | Product Composition of the Tert. Amine | | |
|---|---|---|---|---|---|
| | | | $Me_2NR$ | $R_2NMe$ | $R_3N$ |
| XI A | 99.8 | 96.2 | 96.1 | 2.2 | 1.7 |
| XI B | 99.5 | 95.8 | 96.8 | 2.2 | 1.0 |
| XI C | 99.4 | 95.5 | 97.2 | 1.7 | 1.1 |
| XI D | 99.7 | 96.0 | 97.1 | 2.0 | 0.9 |

| Catalyst | Alcohol Conversion | Content of Tert. Amine (Weight Percent) | Product Composition of the Tert. Amine | | |
|---|---|---|---|---|---|
| | | | Me$_2$NR | R$_2$NMe | R$_3$N |
| XI E | 99.6 | 96.1 | 96.7 | 2.1 | 1.1 |

What is claimed is:

1. A method as in claim 8 wherein said alcohol is a primary alcohol having from 6 to 22 carbon atoms.

2. A method as in claim 1 wherein said alcohol is an aliphatic alcohol having from 10 to 18 carbon atoms.

3. A method as in claim 1 wherein an aldehyde is reacted.

4. A process as in claim 1 wherein said amine is a primary alkylamine or a secondary dialkylamine having from 1 to 4 carbon atoms in each alkyl, or is a mixture thereof.

5. A method as in claim 4 wherein said amine is monomethylamine or dimethylamine.

6. A method as in claim 8 wherein said catalyst consists of oxides and/or hydroxides of copper and tin in a molar ratio from 0.1:1 to 10:1.

7. A method as in claim 6 wherein the molar ratio of copper to tin is from 1.5:1 to 5.5:1.

8. A method for making an amine which comprises reacting a member of the group consisting of alcohols and aldehydes having up to 26 carbon atoms with ammonia or with a primary and/or secondary amine having from 1 to 26 carbon atoms, at an elevated temperature, in the liquid phase, and in the presence of an unsupported catalyst consisting of a combination of copper and tin compounds activated with an organometallic reducing agent.

* * * * *